(12) United States Patent
Boveja et al.

(10) Patent No.: US 6,505,074 B2
(45) Date of Patent: Jan. 7, 2003

(54) METHOD AND APPARATUS FOR ELECTRICAL STIMULATION ADJUNCT (ADD-ON) TREATMENT OF URINARY INCONTINENCE AND UROLOGICAL DISORDERS USING AN EXTERNAL STIMULATOR

(76) Inventors: Birinder R. Boveja, 8879 S. Chestnut Hill Way, Highlands Ranch, CO (US) 80130; Angely Widhany, 8879 S. Chestnut Hill Way, Highlands Ranch, CO (US) 80130

( * ) Notice: Subject to any disclaimer, the term of this patent is extended or adjusted under 35 U.S.C. 154(b) by 0 days.

(21) Appl. No.: 09/752,083

(22) Filed: Dec. 29, 2000

(65) Prior Publication Data

US 2001/0002441 A1 May 31, 2001

Related U.S. Application Data

(63) Continuation-in-part of application No. 09/178,060, filed on Oct. 26, 1998, now Pat. No. 6,205,359.

(51) Int. Cl.$^7$ .................................................. A61N 1/32
(52) U.S. Cl. .................................. 607/41; 128/DIG. 25
(58) Field of Search ............................... 607/40, 41, 39; 128/DIG. 25

(56) References Cited

U.S. PATENT DOCUMENTS

| 3,796,221 | A |   | 3/1974 | Hagfoes et al. ............. 128/421 |
| 3,870,051 | A | * | 3/1975 | Brindley ....................... 607/40 |
| 4,607,639 | A | * | 8/1986 | Tanagho et al. .............. 607/40 |
| 4,771,779 | A |   | 9/1988 | Tanagho et al. ........ 128/419 E |
| 5,304,206 | A |   | 4/1994 | Baker et al. ................... 607/2 |
| 6,055,456 | A |   | 4/2000 | Gerber et al. ............... 607/117 |

* cited by examiner

Primary Examiner—Jeffrey R. Jastrzab

(57) ABSTRACT

An apparatus and method for neuromodulation therapy for urinary incontinence and urological disorders comprises an implantable lead-receiver, and an external stimulator having a power source, controlling circuitry, and predetermined programs. The stimulator further includes a primary coil which inductively transfers electrical signals to the lead-receiver, which is also in electric contact with the sacral nerves. The external stimulator emits electrical pulses to stimulate the sacral plexus according to a predetermined program. In a second mode of operation, an operator may manually override the predetermined sequence of stimulation.

21 Claims, 13 Drawing Sheets

METHOD AND APPARATUS FOR ELECTRICAL STIMULATION ADJUNCT (ADD-ON) TREATMENT OF URINARY INCONTINENCE AND UROLOGICAL DISORDERS USING AN EXTERNAL STIMULATOR

This is a Continuation-in-Part application claiming priority from pending prior application Ser. No. 09/178,060 filed Oct. 26, 1998, the prior application being incorporated herein by reference now U.S. Pat. No. 6,205,359. Further, it is related to application Ser. No. 09/751,966 filed Dec. 29, 2000 entitled AN EXTERNAL STIMULATOR FOR ADJUNCT (ADD-ON) TREATMENT FOR NEUROLOGICAL, NEUROPSYCHIATRIC, AND UROLOGICAL DISORDERS now U.S. Pat. No. 6,366,814.

FIELD OF THE INVENTION

The present invention relates to electrical neuromodulation therapy for medical disorders, more specifically neuromodulation therapy for urinary incontinence and urological disorders utilizing an implanted lead-receiver and external stimulator containing predetermined programs.

BACKGROUND OF THE INVENTION

Biological and human clinical research has shown utility of electrical nerve stimulation for urinary incontinence and a broad group of urological disorders. This invention is directed to the adjunct therapy for these disorders utilizing an implanted lead-receiver and an external stimulator with predetermined stimulation programs.

In considering the background of urinary urge incontinence, FIG. 1 shows a sagittal section of the human female pelvis showing the bladder 10 and urethra 13 in relation to other anatomic structures. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder and urethra are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanoreceptors trigger a coordinated micturition reflex via a center in the upper pons 88, as depicted schematically in FIG. 2. The reflex detrusor 92 (muscle in the wall of the urinary bladder) contraction generates an increased bladder pressure and an even stronger activation of the mechanoreceptors. Their activity in turn reinforces the pelvic motor output to the bladder, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 90, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the postganglionic neurons in the vesical ganglia and directly on the detrusor muscle of the bladder 92. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneously. The symptomatic pattern also usually is consistent over long periods.

Based on clinical experience, subtypes of urinary incontinance include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency. Electro stimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that uses electrical stimulation of the sacral nerves, (a general diagram of spinal cord and sacral nerves 85 is shown in FIG. 3). The aim of this treatment modality is to achieve detrusor 92 inhibition by chronic electrical stimulation of afferent somatic sacral nerve fibers 85 via implanted electrodes coupled to a subcutaneously placed pulse generation means.

The rationale of this treatment modality is based on the existence of spinal inhibitory systems that are capable of interrupting a detrusor 92 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 85. Of the sacral nerve roots the S3 root is the most practical for use in chronic electrical stimulation.

Most nerves in the human body are composed of thousands of fibers, of different sizes designated by groups A, B and C, which carry signals to and from the brain. The vagus nerve 54, for example, may have approximately 100,000 fibers of the three different types, each carrying signals. Each axon or fiber of that nerve conducts only in one direction, in normal circumstances. The A and B fibers are myelinated (i.e., have a myelin sheath, constituting a substance largely composed of fat, whereas the C fibers are unmyelinated.

A commonly used nomenclature for peripheral nerve fibers, using Roman and Greek letters, is given in the table below:

| Group | External Diameter (μm) | Conduction Velocity (m/sec) |
|---|---|---|
| Myelinated Fibers | | |
| Aα or IA | 12–20 | 70–120 |
| Aβ:IB | 10–15 | 60–80 |
| II | 5–15 | 30–80 |
| Aγ | 3–8 | 15–40 |
| Aδ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

In neuromodulation, the entire innervation system should be intact. As shown schematically in FIG. 5, the procedure consists of placing electrodes 61,62 in one of the sacral foraman as close to the pelvic plexus and pudendal nerve as possible and connecting the lead 59 with a means for electrical stimulation 49. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus in the brain. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branhes of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 85. Sacral nerve 85 stimulation is based on research dedicated to the understanding of the voiding reflex as well as the role and influence of the sacral nerves 85 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 85.

Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibiton in this setting, though data supporting this hypotheses are lacking.

In summary, the rationale for neuromodulation in the management of such patients is the observation that stimulation of the sacral nerves via electrical stimulation can inhibit inappropriate neural reflex behavior.

PRIOR ART

Prior art electrical neuromodulation for urinary incontinence, is generally directed to the use of an implantable lead and an implantable pulse generator technology or "cardiac pacemaker like" technology. In the prior art, the pulse generator is programmed via a "personnel computer (PC)" based programmer that is modified and adapted with a programmer wand which is placed on top of the skin over the pulse generator implant site. Each parameter is programmed independent of the other parameters. Therefore, millions of different combinations of programs are possible. In the current application, limited number of programs are pre-selected.

U.S. Pat. No. 4,771,779 (Tanagho et al) is directed to a system for controlling bladder evacuation, which consists of multiple implanted stimulation systems having electrodes positioned on nerves controlling external sphincter and bladder functions, and electronic control system which transmit to the stimulation systems. In this patent, by having multiple stimulation systems and means of controlling them, the interaction between stimulating the bladder and external sphincter can be controlled.

U.S. Pat. No. 6,055,456 (Gerber) is generally directed to an implantable medical lead for stimulation of sacral nerves. The lead containing a distal and a proximal electrode.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current invention, where consistent therapy needs to be continuously sustained over a prolonged period of time. The methodology disclosed is focused on circuitry within the receiver, which would not be sufficient when the transmitting coil and receiving coil assume significantly different orientation, which is likely in the current application. The present invention discloses a novel approach for this problem.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet and tapping sequence.

The advantage of the apparatus and method as described in this application is that the patient is able, within limits, to select and alter a program for their comfort without going to the physician's office. Such a system is also cheaper for the patient, as it can be manufactured for a fraction of the cost of an implantable pulse generator. Additionally, since the implanted circuit does not have a battery implanted, this eliminates the need for surgical replacement as in an implantable pulse generator.

SUMMARY OF THE INVENTION

The present invention is directed to system and methods for adjunct electrical neuromodulation therapy for urinary incontinence and neuro-urological disorders using predetermined programs with an external stimulator. The system consists of an implantable lead-receiver containing passive circuitry, electrodes adapted for stimulation of sacral plexus or, and a coil for coupling to the external stimulator. The external stimulator, which may be worn on a belt or carried in a pocket contains, electronic circuitry, power source, primary coil, and predetermined programs. The external primary coil and subcutaneous secondary coil are inductively coupled.

In one aspect of the invention the pulse generator contains a limited number of predetermined programs packaged into the stimulator, which can be accessed directly without a programmer. The limited number of programs can be any number of programs even as many as 50 programs, and such a number is considered within the scope of this invention.

In another feature of the invention, the system provides for proximity sensing means between the primary (external) and secondary (implanted) coils. Utilizing current technology, the physical size of the implantable lead-receiver has become relatively small. However, it is essential that the primary (external) and secondary (implanted) coils be positioned appropriately with respect to each other. The sensor technology incorporated in the present invention aids in the optimal placement of the external coil relative to a previously implanted subcutaneous coil. This is accomplished through a combination of external and implantable or internal components.

In another feature of the invention, the external stimulator has predetermined programs, as well as a manual "ON" and "OFF" button. Each of these programs has a unique combination of pulse amplitude, pulse width, frequency of stimulation, "ON" time and "OFF" time. After the therapy has been initiated by the physician, the patient or caretaker has a certain amount of flexibility for adjusting the therapy (level of stimulation). The patient has the flexibility to decrease (or increase) the level of stimulation (within limits). The manual "ON" button gives the patient flexibility to immediately start the stimulating pattern at any time. Of the pre-determined programs, patients do not have access to at least one of the programs, and the locked out programs can be activated only by the physician. The physician can activate the patient "locked-out" programs either in person or via the internet using a cable modem and an external controller using an Ethernet interface as described in a copending application.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

The system and method of programmed neuromodulation in this invention consists of an implantable lead-receiver and an external stimulator with predetermined programs of stimulation. The implantable lead-receiver and external stimulator are inductively coupled. The predetermined programs contain unique combination of parameters which differ in the aggressiveness of the therapy. Some of the predetermined programs may be "locked-out" to the patient or caretaker, and can be accessed and controlled by the physician only.

Figure 1:
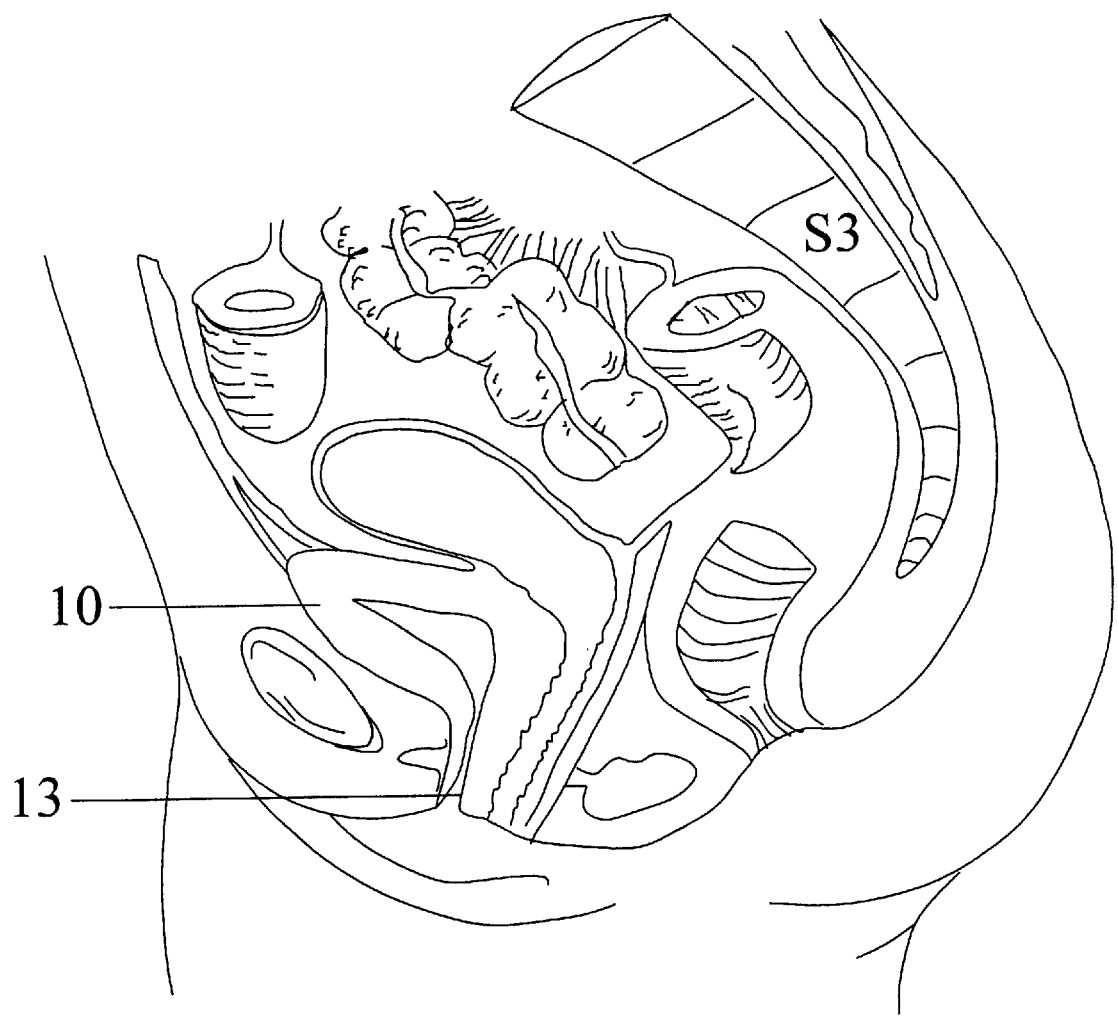
FIG. 1 shows a diagram of the sagittal section of the female pelvis, showing the relationship between various anatomic structures.
Figure 2:
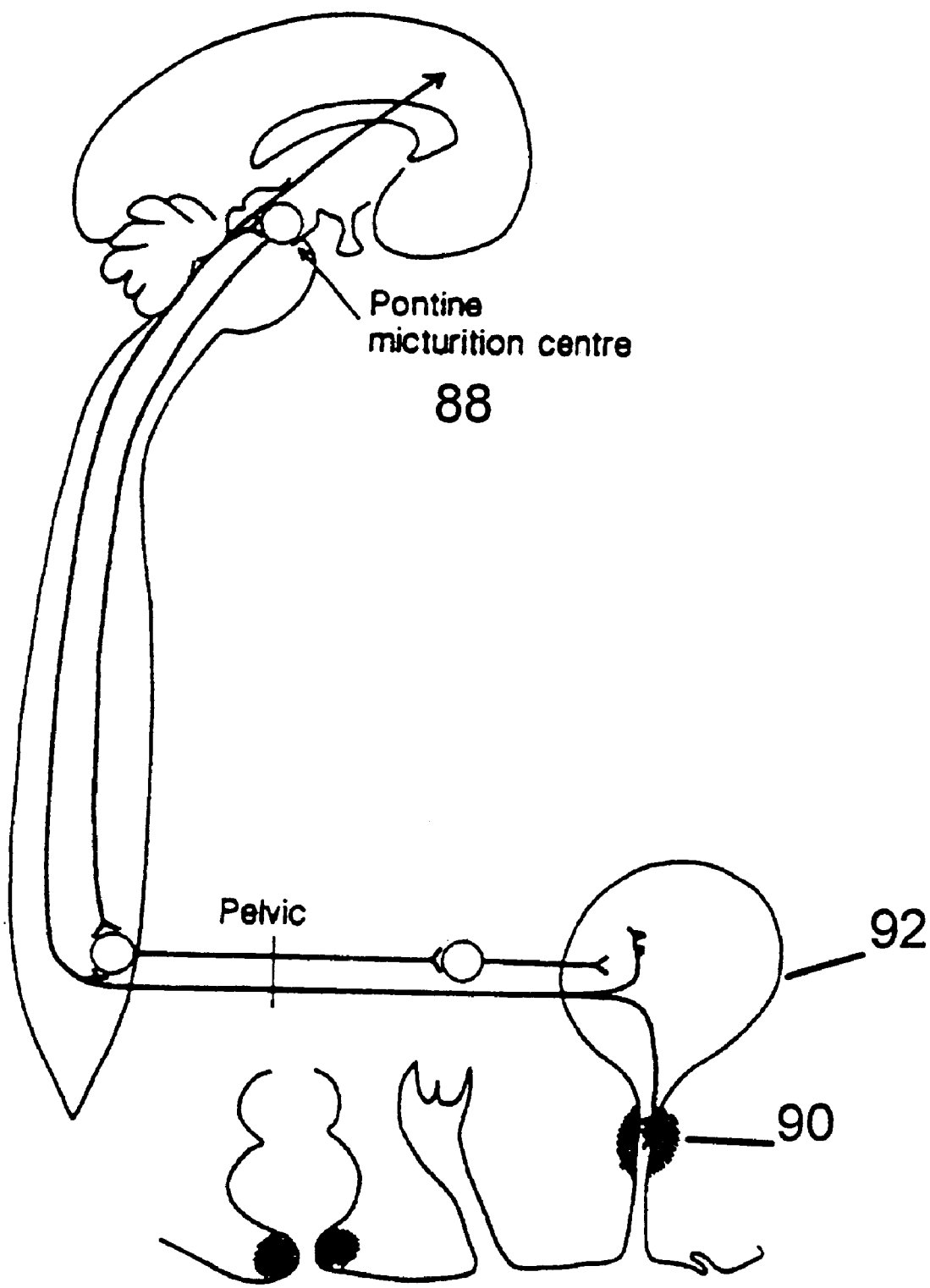
FIG. 2 is a schematic diagram showing physiological control of micturition.
Figure 3:
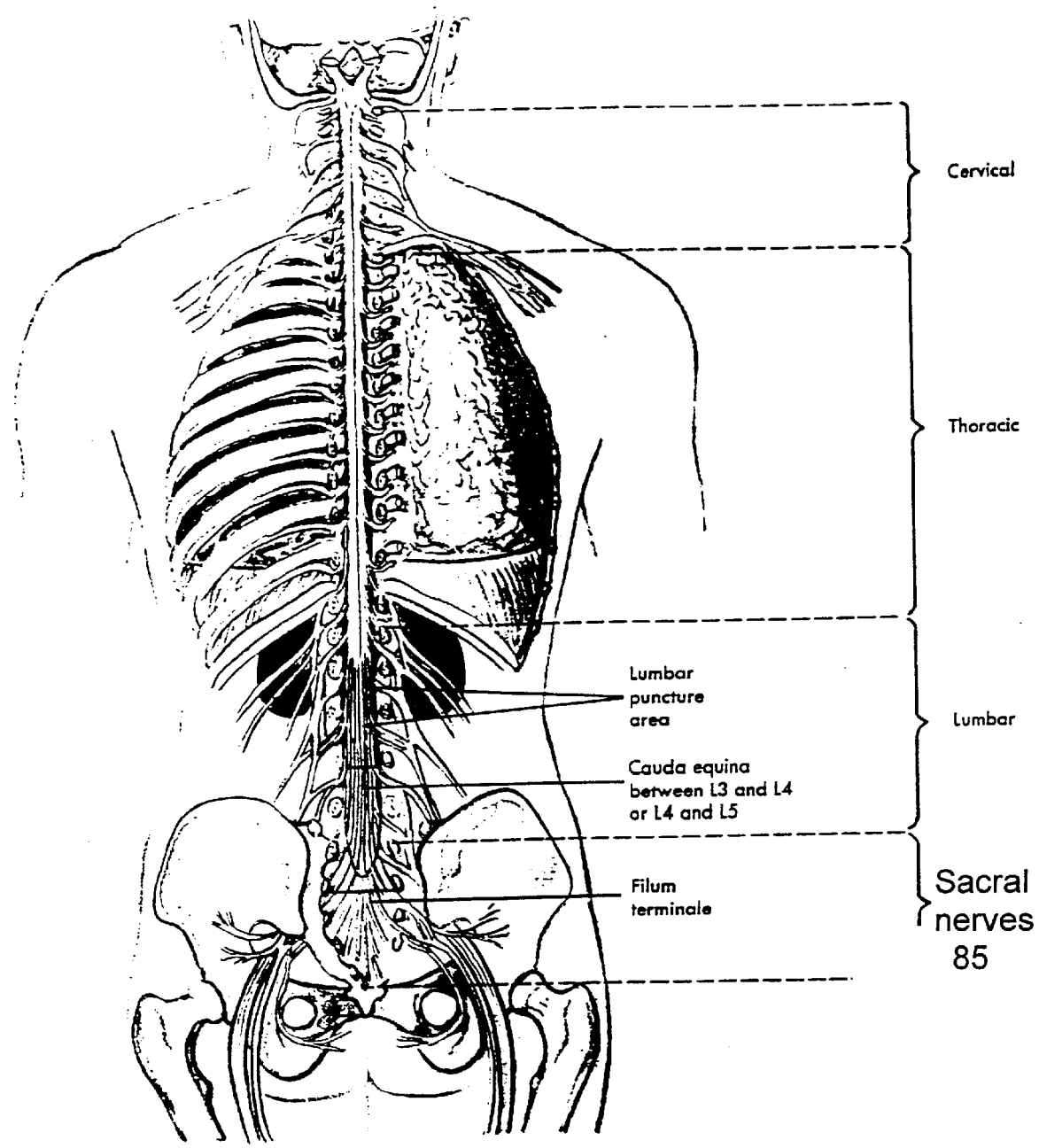
FIG. 3 is a diagram showing anatomic relationships of spinal nerves and sacral plexus.
Figure 4:
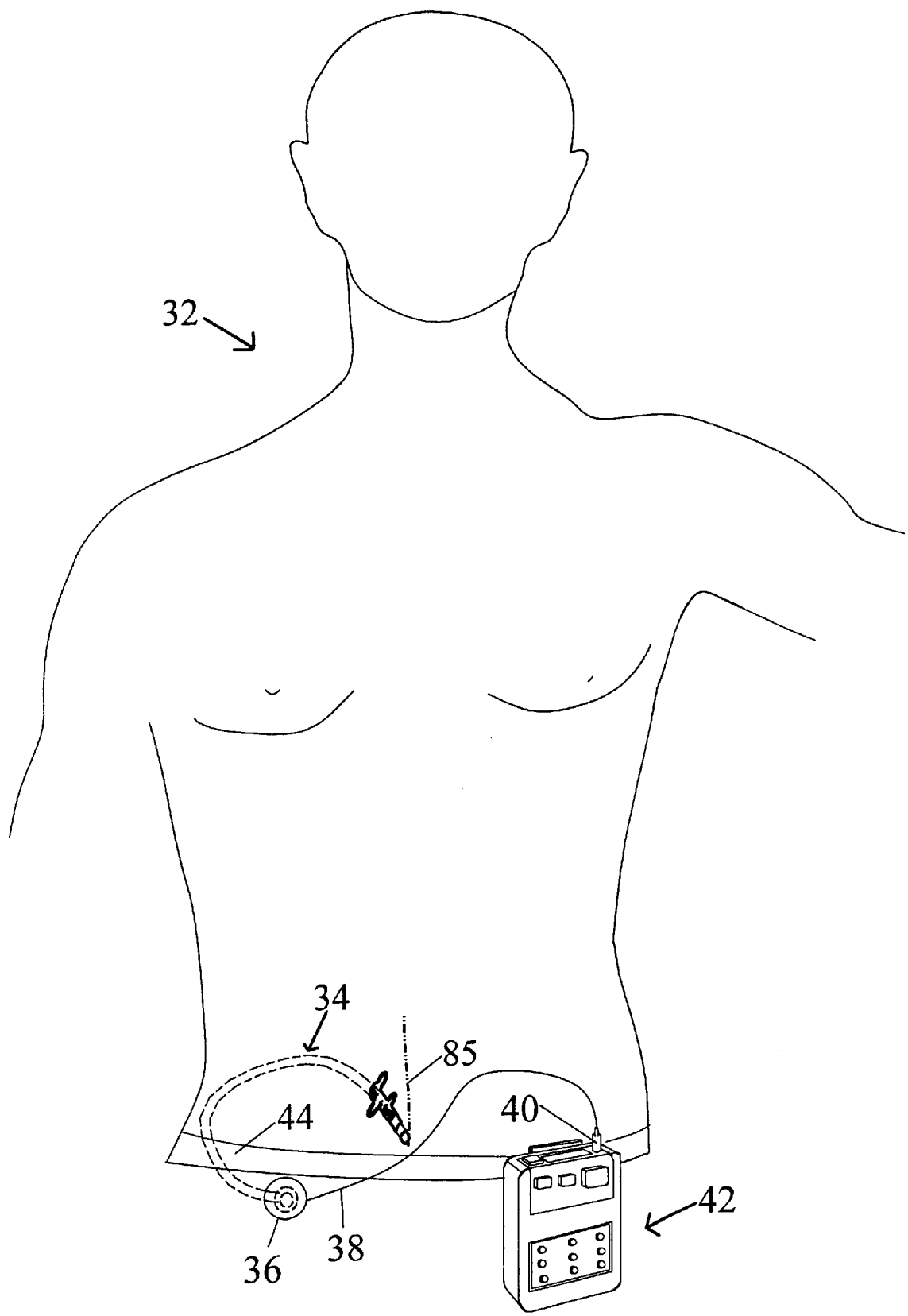
FIG. 4 is a diagram of a patient wearing an external stimulator on a belt.
Figure 5:
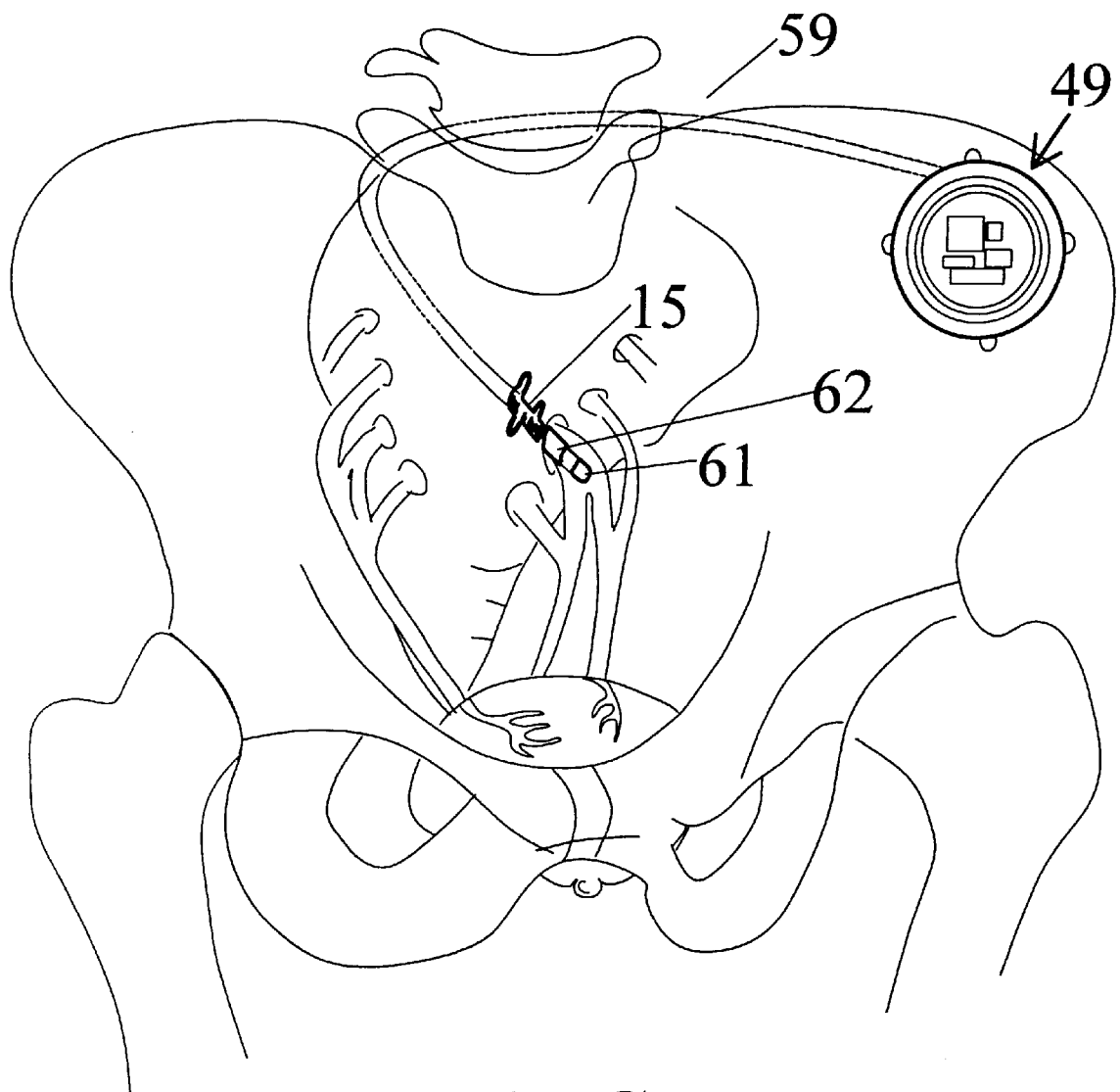
FIG. 5 is a schematic diagram of the sacral region showing electrodes in sacral foraman, and placement of the lead-receiver.

Referring now to the drawings, FIG. 4 shows a schematic diagram of a patient 32 with an implantable lead-receiver 34 and an external stimulator 42, clipped on to a belt 44 in this case. The external stimulator 42 may alternatively be placed in a pocket or other carrying device. The primary (external) coil 46 of the external stimulator 42 is inductively coupled to the secondary (implanted) coil 48 of the implanted lead-receiver 34. The implantable lead-receiver 34 has circuitry at the proximal end, and has two stimulating electrodes at the distal end. As shown in FIG. 5, the negative electrode (cathode) 61 is positioned at the distal end and the positive electrode (anode) 62 is positioned away from the distal end 62, and is pulled back from the tip slightly. During the surgical implant procedure, the stimulating electrodes are tunneled subcutaneously and the electrodes are placed in the foraman of the sacral nerve 85 and the lead receiver is implanted subcutaneously and held in place by tying sutures to the suture sleeve 15. The incisions are surgically closed and the chronic stimulation process can begin when the tissues are healed from the surgery.

Figure 6:
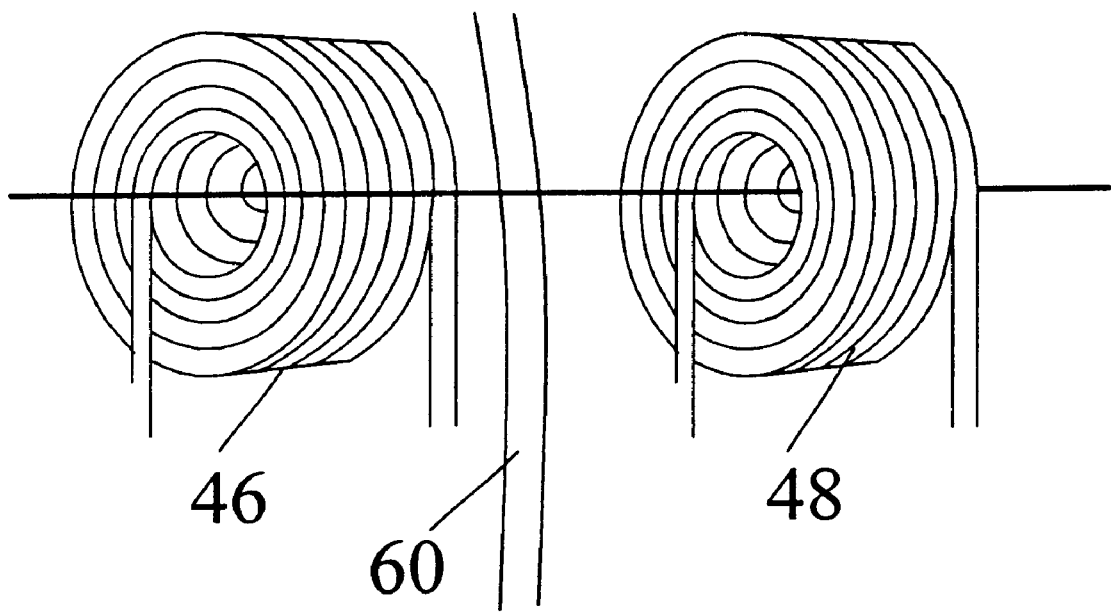
FIG. 6 is a diagram showing two coils along their axis in a configuration such that the mutual inductance would be maximum.

For therapy to commence, the primary (external) coil 46 is placed on the skin on top of the surgically implanted (secondary) coil 48. An adhesive tape is then placed on the skin 60 and external coil 46 such that the external coil 46 is taped firmly to the skin 60. For efficient energy transfer to occur, it is important that the primary (external) and secondary (internal) coils 46,48 be positioned along the same axis and be optimally positioned relative to each other (FIG. 6). In the present embodiment, the external coil 46 is connected to proximity sensing circuitry 50. The correct positioning of the external coil 46 with respect to the internal coil 48 is indicated by turning ON of a light emitting diode (LED) on the external stimulator 42.

Figure 7:
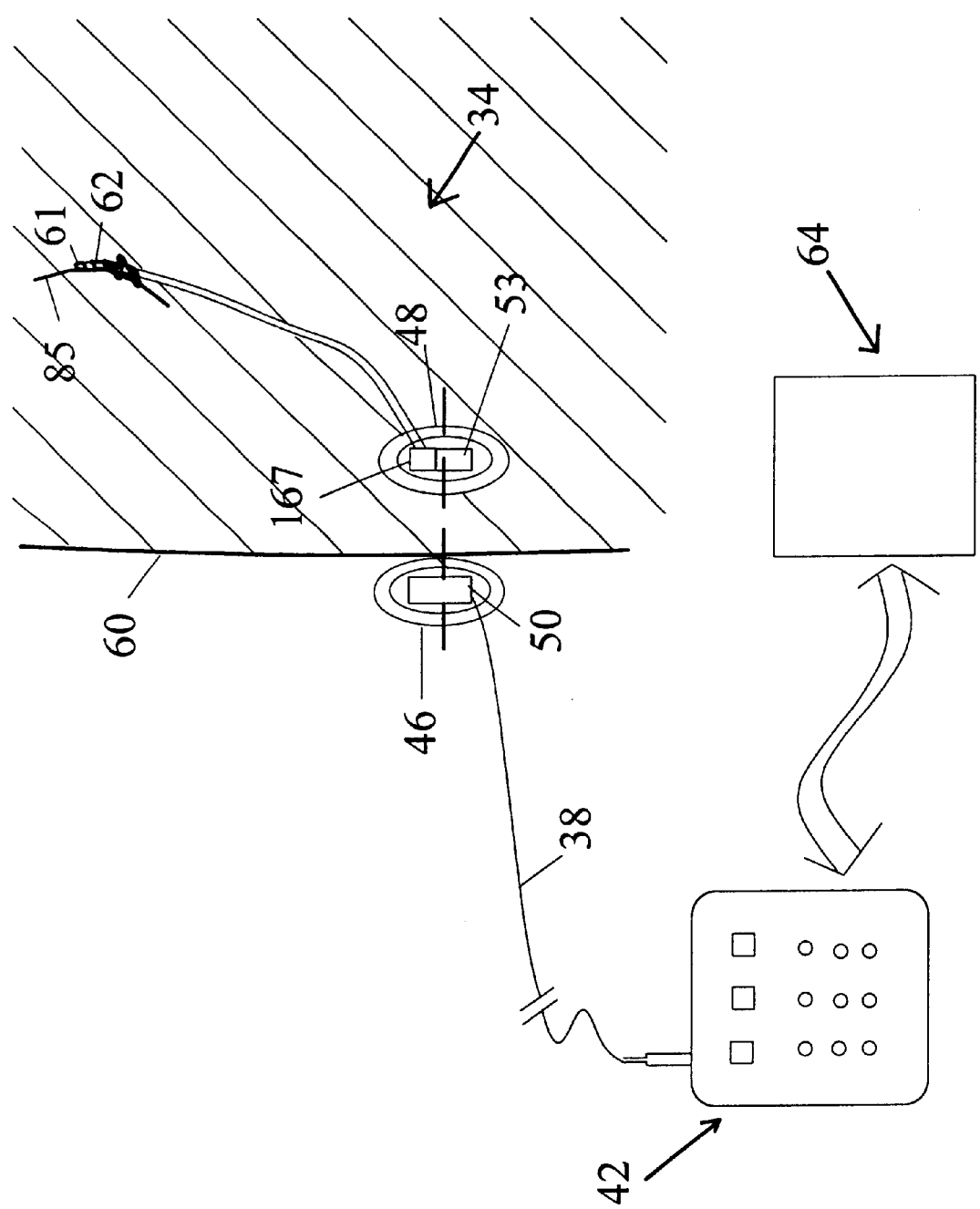
FIG. 7 shows external stimulator coupled to the implanted unit.

Optimal placement of the primary (external) coil 46 is done with the aid of proximity sensing circuitry incorporated in the system. The proximity sensing occurs utilizing a combination of external and implantable or internal sensing components. The internal components contains a relatively small magnet composed of materials that exhibit Giant Magneto-Resistor characteristics such as Samarium-cobalt, passive circuitry and a coil. As depicted in FIG. 7, the external coil 46 contains proximity sensor circuitry 50 that is rigidly connected in a convenient enclosure mounted supercutaneously. The sensors measure the direction of the field applied from the magnet to sensors within a specific range of field strength magnitude. The dual sensors exhibit accurate sensing under relatively large separation between the sensor and the target magnet. As the external coil 46 placement is "fine tuned", the condition where the supercutaneous external (primary) coil 46 comes in optimal position and is located adjacent and parallel to the subcutaneous (secondary) coil 48, along its axis, is recorded and indicated by a light emitting diode (LED) on the external stimulator 42.

Figure 8:
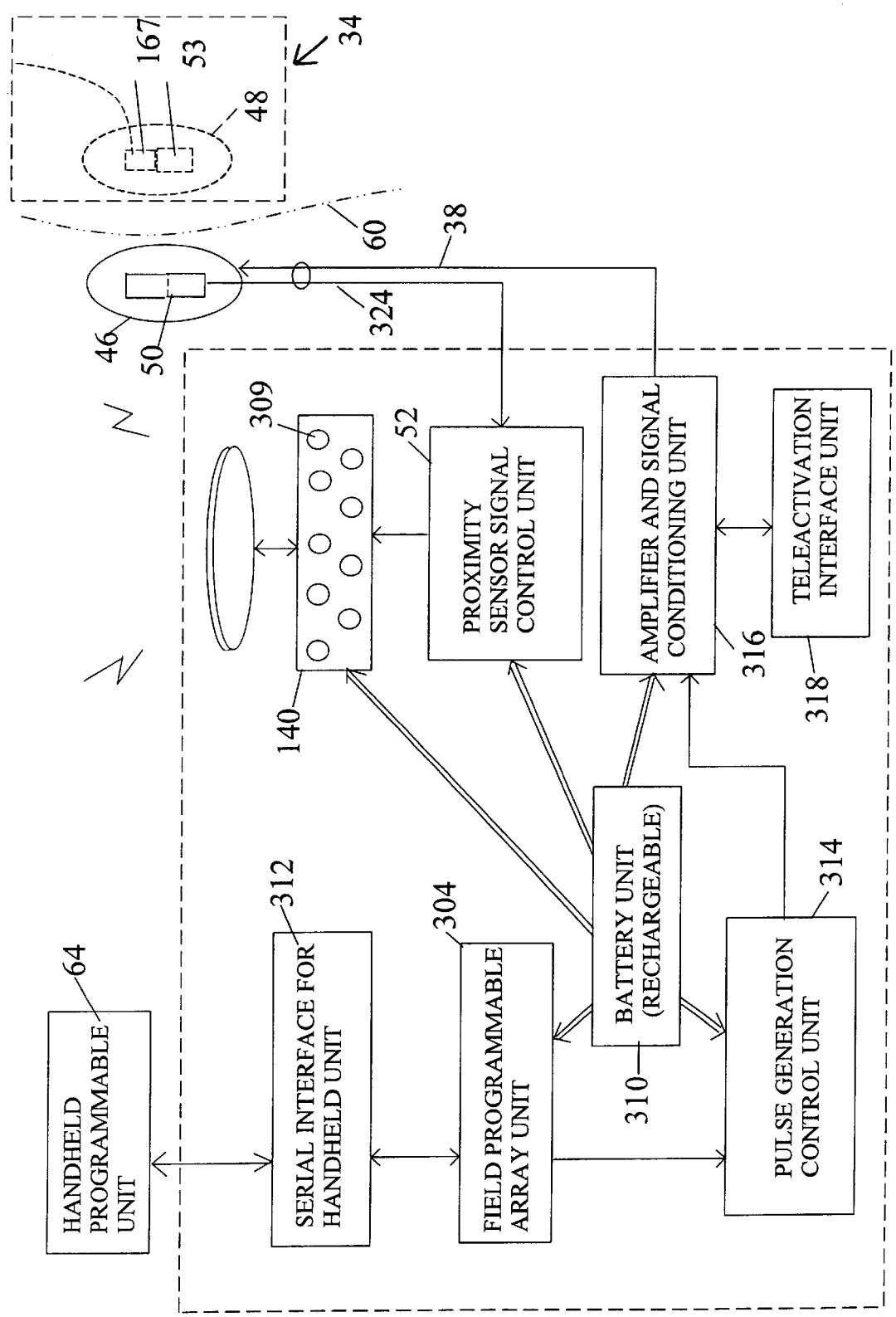
FIG. 8 shows the block diagram for the external stimulator.

FIG. 8 shows an overall block diagram of the external stimulator 42. The proximity sensing components are the primary (external) coil 46, supercutaneous (external) proximity sensors in the proximity sensor circuit unit 50, and a subcutaneous secondary coil 48 with a Giant Magneto Resister (GMR) magnet 53 associated with the proximity sensor unit. The proximity sensor circuit 50 provides a measure of the position of the secondary implanted coil 48. The signal output from proximity sensor circuit 50 is derived from the relative location of the coils. The coil subassemblies consist of the coil and the associated electronic components, that are rigidly connected to the coil.

The proximity sensors (external) contained in the proximity sensor circuit 50 detect the presence of a GMR magnet 53, composed of Samarium Cobalt, that is rigidly attached to the subcutaneous secondary coil 48. The proximity sensors are mounted externally as a rigid assembly and sense the actual separation between the coils, also known as the proximity distance. In the event that the distance exceeds the theoretical limit, the signal drops off and an alarm sounds to indicate failure of the production of adequate signal in the secondary implant circuit 167, as applied in the present embodiment of the device. This signal is provided to the location indicator LED 140. The programmable parameters are stored in a programmable logic 304.

Figure 9:
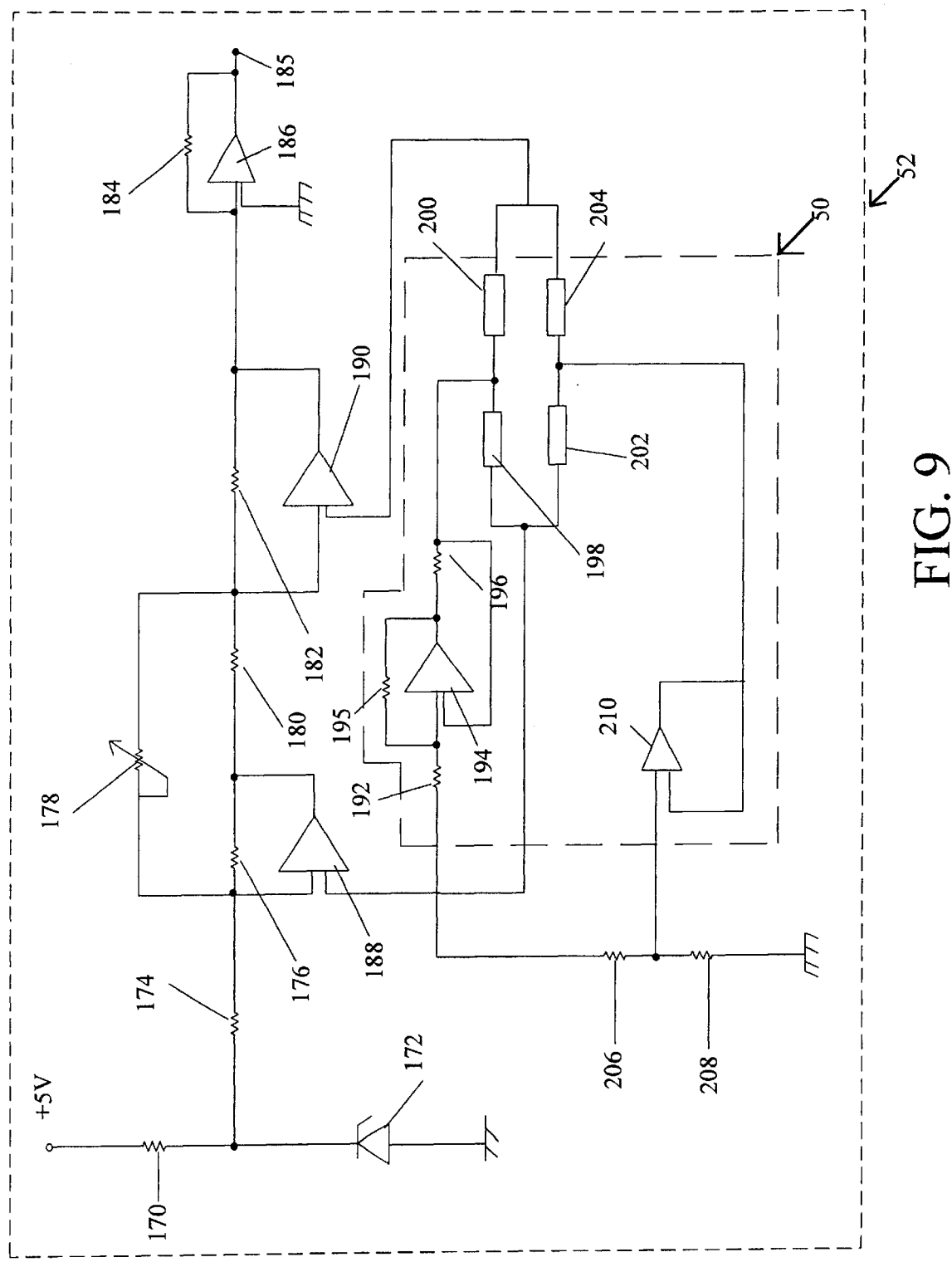
FIG. 9 shows the GMR sensor amplification unit.

FIG. 9 shows the circuit used to drive the proximity sensors of the proximity sensor circuit. The two proximity sensors 198, 202 obtain a proximity signal based on their position with respect to the implanted GMR magnet 53. This circuit also provides temperature compensation. The sensors 198, 202 are 'Giant Magneto Resistor' (GMR) type sensors packaged as proximity sensor unit 50. There are two components of the complete proximity sensor circuit 51. One component is mounted supercutaneously 50 and the other component is mounted in the remote control unit 42. The resistance effect depends on the combination of the soft magnetic layer of magnet 53, where the change of direction of magnetization from external source can be large, and the hard magnetic layer, where the direction of magnetization remains unchanged. The resistance of this sensor varies along a straight motion through the curvature of the magnetic field. A bridge differential voltage is suitably amplified and used as proximity signal.

The Siemens GMR B6 (Siemens Corp., Special Components Inc. New Jersey) is used for this function in the present embodiment. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 198, 202 are oriented orthogonal to each other.

The distance between the magnet and sensor is not relevant as long as the magnetic field is between 5 and 15 KA/m, and provides a range of distances between the sensors 198, 202 and the magnetic material 53. The GMR sensor registers the direction of the external magnetic field. A typical magnet to induce permanent magnetic field is approximately 15 by 8 by 5 mm$^3$, for this application and these components. However, the sensors 198, 202 are sensitive to temperature, such that the corresponding resistance drops as temperature increases. This effect is quite minimal until about 100° C. A full bridge circuit is used for temperature compensation, as shown in temperature compensation circuit 50 of FIG. 9. The sensors 198, 202 and a pair of resistors 200, 204 are shown as part of the bridge network for temperature compensation. It is also possible to use a full bridge network of two additional sensors in place of the resistors 200, 204.

The signal from either proximity sensor 198, 202 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees.

The remote circuit package is shown in FIG. 8 and indicator unit 140 is provided to indicate following conditions: low battery state (if external battery is low), program number in use, proximity distance too large or coil proximity failure (for situations where the patch containing the external coil 46, has been removed, or is twisted abnormally etc.). Indication is also provided to assist the placement of the patch. In case of general failure, a red light with audible signal is provided when the signal is not reaching the subcutaneous circuit. The information on the low battery, normal and out of power conditions will forewarn the user of the requirements of any corrective actions.

Figure 10:
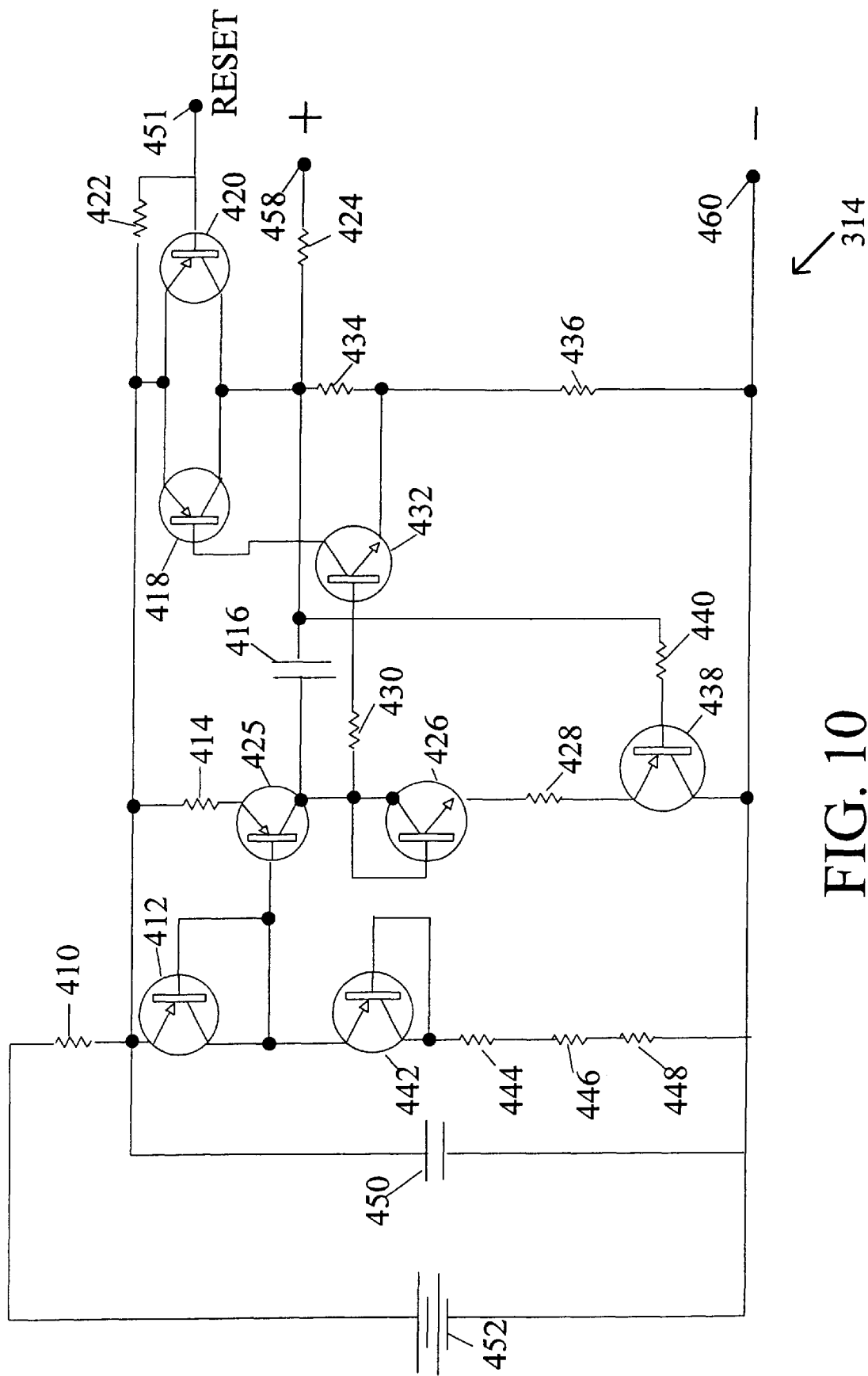
FIG. 10 shows the pulse generator circuit.

The pulse generator circuitry, shown schematically in FIG. 10, exhibits typical multivibrator functionality. This circuit produces regularly occurring pulses where the amplitude, pulse width and frequency is adjustable. The battery 452 is the main external power source for this circuit and can derive from the rechargeable battery 310 (shown in FIG. 9). The capacitor 450 is connected in parallel with the battery 452. The combination of transistors 412, 442 and 425, and resistors 410, 444, 446 and 448 acts as a constant current source generated at the collector of transistor 426. The transistor 412 has collector connected to the emitter of transistor 442 and base of transistor 425. The transistors 412 and 442 are connected to provide a constant voltage drop. Likewise, transistor 426 also acts as a diode with a resistor 428 connected in series and further connected to the negative terminal of the line at terminal 460. Capacitor 416 provides timing characteristics and its value helps determine pulse width and pulse frequency. The output of the oscillator appears at terminal 458.

Initially, the capacitor 416 gets charged with current from the path of resistor 434 and 436 while all the transistors are turned off. As the capacitor charges up transistor 432 will become forward biased and current will flow via resistors 430 and 436 from the base to emitter resistors. This action turns on the transistor 418 and the positive voltage from the power supply 452 is made available at the base of transistor 438 through resistor 440. This results in the transistor 438 getting turned on. The conduction of transistor 438 causes capacitor 416 to discharge. The time constant for the charge and discharge of capacitor 416 is determined by value of the resistors 428 and 440 and capacitor 416. After the time constant, transistor 432 turns off, and this in turn turns off transistors 438 and 418. A reset mechanism for this multivibrator can be provided by setting a positive voltage, for example 2.5 volts, to the base of transistor 420. This positive increase in voltage turns on transistor 420 followed by transistor 438. The turning on of transistor 438 discharges the capacitor 416 and the reset operation is complete.

Figure 11:
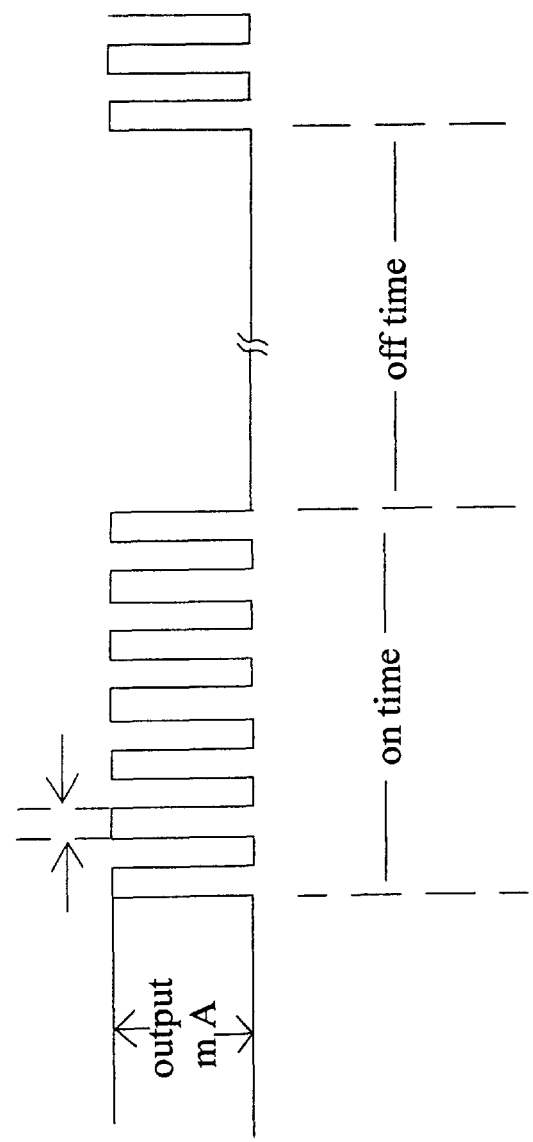
FIG. 11 shows the pulse train to be transmitted to the implant unit.
Figure 12:
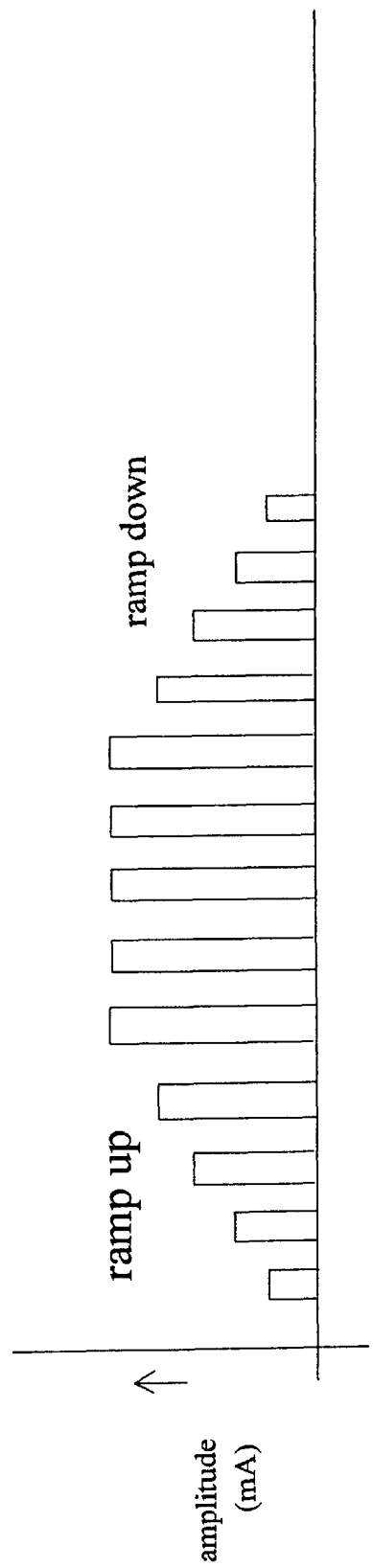
FIG. 12 shows the ramp-up and ramp-down characteristic of the pulse train.

FIG. 11 shows graphically the pulses delivered to the nerve tissue for therapy. As shown in FIG. 12, for patient comfort when the electrical stimulation is turned on, the electrical stimulation is ramped up and ramped down, instead of abrupt delivery of electrical pulses.

The external stimulator 42 contains several predetermined programs that comprise a unique combination of pulse amplitude, pulse width, frequency of stimulation, ON time and OFF time. The various predetermined programs represent varying degrees of aggressiveness of the stimulation therapy. At least one of these programs may be "locked-out" to the patient. The physician can activate the patient "locked out" programs, either in person by accessing the programs via a handheld programmable unit 64 (FIGS. 7 and 8), or activate the programs remotely via the internet cable connection as described in a copending application. The number of predetermined programs can be as many as 50 programs, and such a number is considered within the scope of the invention. In order to keep the number of programs convenient for the patient, the presently preferred embodiment contains nine predetermined programs that are arranged in such a way that the aggressiveness of the stimulation (therapy) increases from program #1 to program #2 and so on.

The following are examples of least aggressive therapy.

Program: 1.5 volt output, 0.2 msec pulse width, 10 Hz frequency, 30 sec ON time, 30 sec OFF time, in repeating cycles.

Program: 2.0 volt output, 0.2 msec pulse width, 15 Hz frequency, 1 minute ON time, 30 sec OFF time, in repeating cycles.

The following are examples of more aggressive level of therapy.

Program: 2.5 volt output, 0.25 msec pulse width, 20 Hz frequency, continuously ON.

Program: 2.5 volt output, 0.3 msec pulse width, 30 Hz frequency, 30 sec ON time, 30 sec OFF time, in repeating cycles.

The following are examples of patient "locked-out" programs.

Program: 3.5 volt output, 0.25 msec pulse width, 25 Hz frequency, 5 minutes ON time, 1 minute OFF time, in repeating cycles.

Program: 4.5 volt output, 0.3 msec pulse width, 30 Hz frequency, 2 minutes ON time, 2 minutes OFF time, in repeating cycles.

The above are examples of the predetermined programs for urinary incontinence applications. The actual parameter settings for any given patient may deviate somewhat from the above.

Figure 13:
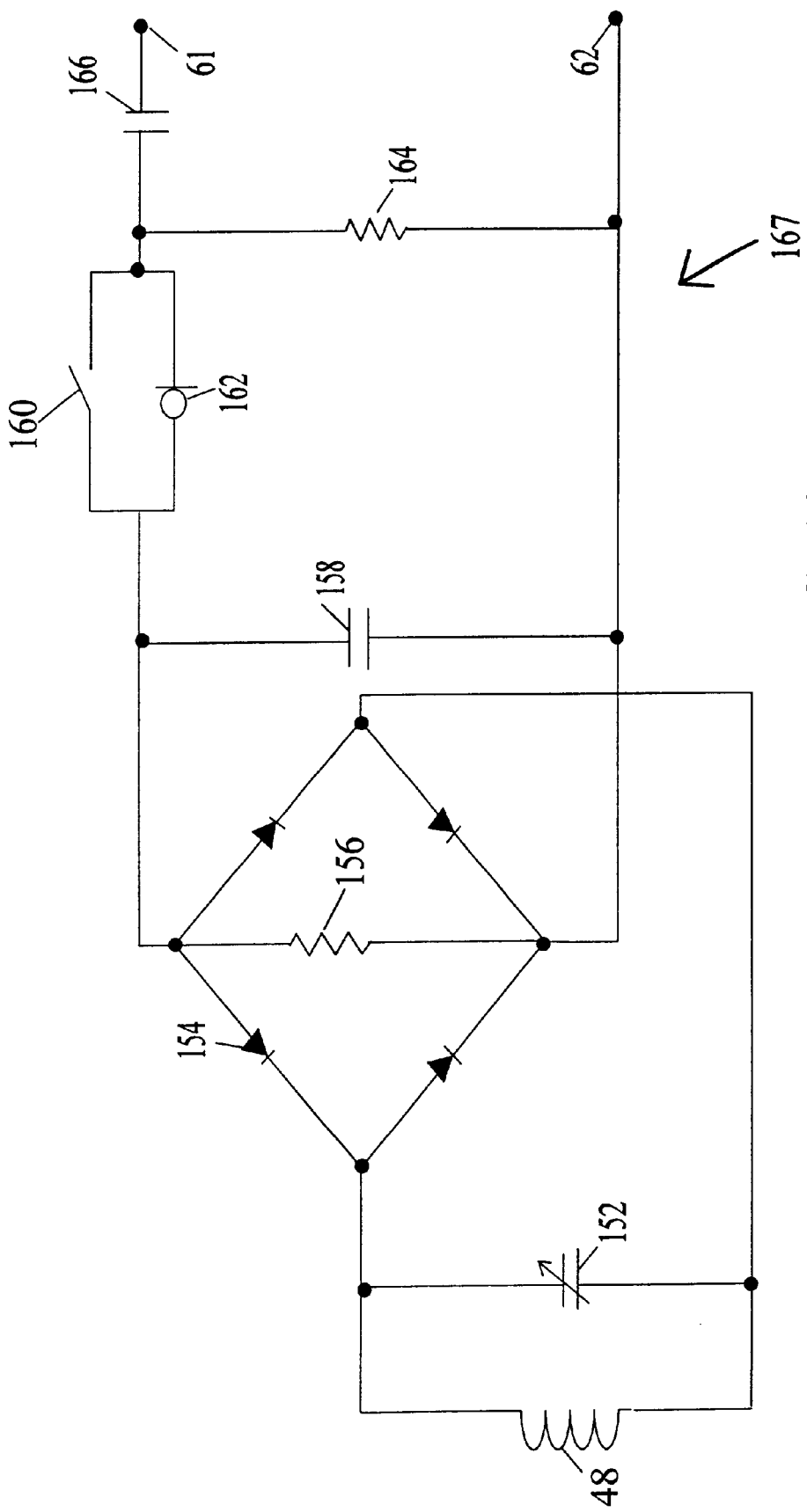
FIG. 13 is a schematic of the passive circuitry in the implanted lead-receiver.

The circuitry contained in the proximal end of the implantable lead-receiver 34 is shown schematically in FIG. 13. In this embodiment, the circuit uses all passive components. Approximately 25 turn copper wire of 30 gauge thickness is used for the primary coil 46 and secondary coil 48. This wire is concentrically wound with the windings all in one plane. A variable capacitor 152 provides flexibility in tuning to the actual frequency received by coil 48 from the primary coil 46. The frequency of the pulse-waveform delivered to the implanted coil 48 can vary and so a variable capacitor 152 provides ability to tune secondary implanted circuit 167 to the signal from the primary coil 46. The pulse signal from implanted coil 48 is rectified by the diode bridge 154 and frequency reduction obtained by capacitor 158 and resistor 164. The last component in line is capacitor 166, used for isolating the output signal from the electrode wire. The return path of signal from cathode 61 will be through anode 62 placed in proximity to the cathode 61 for "Bipolar" stimulation. In the current embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation, and is therefore used in the current embodiment. Unipolar stimulation is more likely to stimulate skeletal muscle in addition to nerve stimulation. The implanted circuit 167 in this embodiment is passive, so a battery does not have to be implanted. It is however possible to implant a battery source for use of active component logic in the implant.

Figure 14:
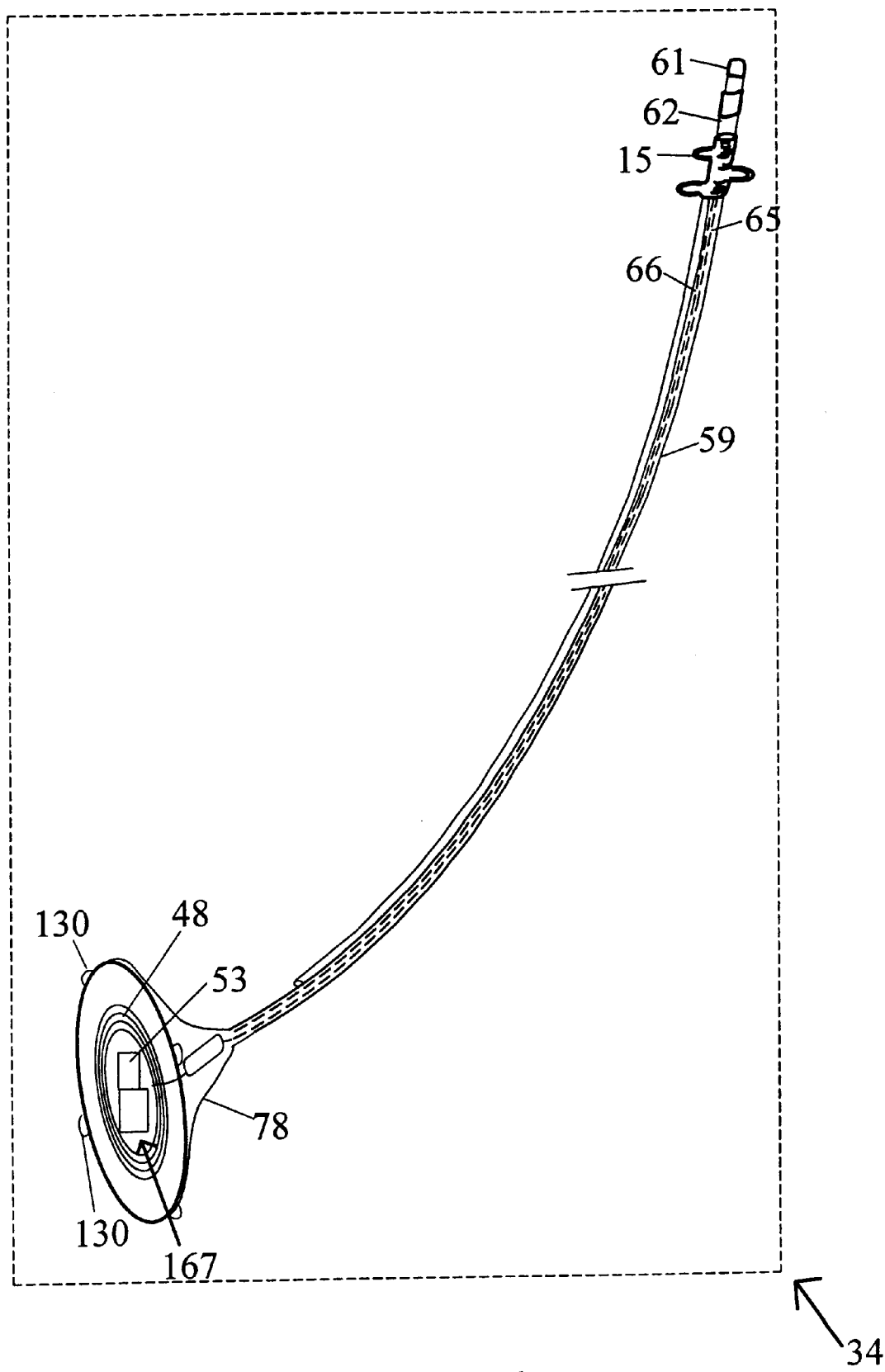
FIG. 14 is a diagram of the implanted lead-receiver for urinary incontinence.

FIG. 14 shows a diagram of the implanted lead-receiver 34 adapted for sacral stimulation. The proximal end 49 is a relatively flat portion and contains the components shown in FIG. 13 on a printed circuit board. The distal end has the two spiral electrodes 61 and 62 for stimulating the nerve. The passive circuitry and electrodes are connected by electrically insulated wire conductors running in the lead body 59 which is made of reinforced medical grade silicone in the presently preferred embodiment.

The fabrication of the lead-receiver 34 is designed to be modular. Thus, several different combinations of the components can be packaged without significantly altering the functionality of the device. As shown in FIG. 14, the lead-receiver 34 components are the proximal end 49 containing coil 48, electrical circuitry 167, and case 78, the lead body 59 containing the conductor 65,66 and the distal end has two electrodes cathode 61 and anode 62. In the modular design concept, several design variables are possible, as shown in the table below.

Table of lead-receiver design variables

| Proximal End Circuitry and Return Electrode | Lead body- Lumens | Lead body- Insulation Materials | Lead-Coating | Conductor (connecting proximal and distal ends) | Electrode- Material | Distal End Electrode- Type |
|---|---|---|---|---|---|---|
| Bipolar | Single | Polyurethane | | Alloy of Nickel-Cobalt | Pure Platinum | Standard ball electrode |
| Unipolar | Double | Silicone | Antimicrobial | | Platinum-Iridium (Pt/IR) Alloy | Hydrogel electrode |
| | Triple | Silicone with Polytetrafluoroethylene (PTFE) | Anti-Inflamatory | | Pt/Ir coated with Titanium Nitride | Steroid eluting |
| | Coaxial | | | | Carbon | |

Either silicone or polyurethane is a suitable material for the implantable lead-receiver body 59. Both materials have proven to have desirable qualities which are not available in the other. Permanently implantable pacemaker leads made of polyurethane are susceptible to some forms of degradation over time. The identified mechanisms are Environmental Stress Cracking (ESC) and Metal Ion Oxidation (MIO). Silicone on the other hand is a softer material, therefore lead body has to be made bigger. In the presently preferred embodiment silicone re-enforced with polytetrafluroethyene (PTFE) is used.

Nerve-electrode interaction is an integral part of this stimulation system. As a practical benefit of the modular design, any type of electrode described below can be used as the distal stimulating electrodes, without changing fabrication methodology or procedure significantly. In the presently preferred embodiment, electrodes made of platinum are used even though platinum-iridium alloys (such as 90% platinum-10% Iridium or 80% platinum-20% Iridium), or carbon could be used as the electrode material. The electrode type could be a hydrogel electrode or a steroid eluting electrode. In a steroid eluting electrode, a small amount of dexamethasone is placed either inside the distal electrode or around the electrode in a silicone collar. Approximately 1 mg dexamethasone is all that is required for the anti-inflammatory action, to lead to a thinner fibrous capsule, and therefore more efficient energy transfer from the electrode to the nerve tissue.

The conductor connecting the circuitry to the stimulating electrodes is made of an alloy of nickel-cobalt. Even though in the present embodiment the lead body is not being coated, in alternative embodiments the finished lead body may be coated with anti-inflammatory or anti-microbial coating to promote better healing after the surgical implant procedure. The coating is independent of fabrication and is performed after the lead-receiver assembly is completed.

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

Various alternatives and embodiments are contemplated as being within the scope of the following claims particularly pointing out and distinctly claiming the subject matter regarded as the invention.

What is claimed is:

1. An apparatus for neuromodulation of the sacral nerves comprising:
    a) an implantable lead-receiver comprising a secondary coil in electrical contact with bipolar electrodes for stimulating a sacral nerve;
    b) an external stimulator comprising a power source, circuitry to emit electrical signals, at least two predetermined programs wherein at least one of the programs is locked out to the patient, and a primary coil;
    c) said primary coil of said external stimulator and said secondary coil of said implantable lead-receiver being capable of forming an electrical connection by inductive coupling;
    whereby said external stimulator controls the neuromodulation of said sacral nerve.

2. The apparatus of claim 1 wherein neuromodulation of said sacral nerves comprises neuromodulation of sacral plexus and its branches.

3. The apparatus of claim 1, wherein said external stimulator comprises a patient override mechanism to manually activate said external stimulator.

4. The apparatus of claim 1, wherein said at least two predetermined programs can be modified to modify the variable component of said electrical signals.

5. The apparatus of claim 1, further comprising a program selection mechanism wherein said at least two predetermined programs may be selectively operated.

6. The apparatus of claim 1 wherein said primary coil of said external stimulator is adapted to be in proximity to the skin of the patient.

7. The apparatus of claim 1, wherein said lead-receiver comprises a lead body with at least one lumen, a lead body insulation, a conductor, at least one electrode and a coil.

8. The apparatus of claim 7 wherein said lead body insulation is selected from the group consisting of polyurethane, silicone and silicone with polytetrafluoroethylene.

9. The apparatus of claim 7 wherein said lead body further comprises a coating selected from the group consisting of lubricious PVP, antimicrobial and anti-inflammatory coatings.

10. The apparatus of claim 7 wherein said electrode comprises a material selected from the group consisting of platinum, platinum/iridium alloy, platinum/iridium alloy coated with titanium nitride and carbon.

11. The apparatus of claim 1, wherein said at least two predetermined programs comprise at least one variable component selected from the group consisting of the current amplitude, pulse width, frequency and on-off timing sequence, and said at least two predetermined programs controls said variable component of said electrical signals.

12. A method to provide therapy for at least one of urinary incontinence, neurourological disorders, bladder control, bladder inflammation, and bladder pain such as may be caused by Interstitial cystitis disease or the like, comprising the steps of:
    a) providing an implantable lead-receiver comprising a secondary coil in electrical contact with bipolar electrodes to stimulate a sacral nerve;
    b) providing an external stimulator comprising a primary coil, power supply, circuitry to emit electrical signals, and at least two predetermined programs to control said electrical signals wherein at least one of the programs is locked out to the patient;
    c) activating one of said at least two programs of said external stimulator to emit said electrical signals to said primary coil; and
    d) inductively transferring said electrical signals from said primary coil of said external stimulator to said secondary coil of said lead-receiver,
    whereby said electrical signals stimulate said sacral nerve with said bipolar electrodes according to at least one of said at least two predetermined programs.

13. The method of claim 12, wherein electrical stimulation of said sacral nerve comprises electrical stimulation of the sacral plexus and its branches.

14. The method of claim 12, further comprising manually controlling said electrical signals to stimulate said sacral nerve.

15. The method of claim 12, wherein
    a) said at least two predetermined programs comprise at least one variable component selected from the group consisting of the current amplitude, pulse width, frequency, and on-off timing sequence; and
    b) said at least two predetermined programs controls said variable component of said electrical signals.

16. The method of claim 12, further comprising manually disengaging said at least two predetermined programs.

17. A method to provide therapy for at least one of urinary incontinence, neurourological disorders, bladder control, bladder inflammation, and bladder pain such as may be caused by Interstitial cystitis disease or the like, comprising the steps of:
    a) providing an implantable lead-receiver comprising a secondary coil in electrical contact with bipolar electrodes to stimulate a sacral nerve;
    b) providing an external stimulator comprising circuitry to emit electrical signals, a primary coil, and power supply;

c) providing at least two programs to control said electrical signals wherein at one of said predetermined programs is controlled by the patient;
d) activating one of said at least two predetermined programs of said external stimulator to emit said electrical signals to said primary coil; and
e) inductively transferring said electrical signals from said primary coil of said external stimulator to said secondary coil of said lead-receiver, whereby said external stimulator stimulates said sacral nerve according to at least one of said at least two predetermined programs.

18. A method for neuromodulating the sacral nerves, comprising:
   a) selecting one of at least two predetermined programs to control the output of an external stimulator;
   b) activating said external stimulator to emit electrical signals in accordance with said one of at least two predetermined programs; and
   c) inductively coupling said external stimulator with an implantable lead-receiver to stimulate a sacral nerve.

19. The method of claim 18, further comprising implanting beneath the skin of a patient said lead-receiver in direct electrical contact with said sacral nerve.

20. The method of claim 12, wherein at least one of said at least two programs is not locked out to the patient.

21. An apparatus for neuromodulation of the sacral nerves comprising:
   a) an implantable lead-receiver comprising a secondary coil in electrical contact with bipolar electrodes to stimulate a sacral nerve;
   b) an external stimulator comprising a power source, circuitry to emit electrical signals, and a primary coil;
   c) at least two predetermined programs to control said electrical signals, wherein at least one of said at least two predetermined programs is controlled by the patient; and
   d) said primary coil of said external stimulator and said secondary coil of said implantable lead-receiver being capable of forming an electrical connection by inductive coupling, whereby said external stimulator is capable of neuromodulating said sacral nerve.

* * * * *